United States Patent [19]

Federer et al.

[11] Patent Number: 5,523,565

[45] Date of Patent: Jun. 4, 1996

[54] USE OF A MASS SPECTROMETER WITH SECONDARY IONIZATION FOR THE INSPECTION OF CONTAINERS

[75] Inventors: Werner Federer, Tulfes; Johannes Villinger, Innsbruck, both of Austria; Peter M. Robertson, Winkel, Switzerland

[73] Assignee: Elpatronic AG, Zug, Switzerland

[21] Appl. No.: 304,130

[22] Filed: Sep. 12, 1994

[30] Foreign Application Priority Data

Sep. 14, 1993 [CH] Switzerland ............. 02747/93

[51] Int. Cl.$^6$ .................................... H01J 49/14
[52] U.S. Cl. ............. 250/281; 250/282; 250/288
[58] Field of Search ........................... 250/281, 283, 250/288; 436/173

[56] References Cited

U.S. PATENT DOCUMENTS

| 4,008,388 | 2/1977 | McLafferty et al. | 250/281 |
| 4,074,475 | 2/1978 | Risby et al. | 250/282 |
| 4,283,626 | 8/1981 | Siegel | 250/282 |
| 4,830,192 | 5/1989 | Plester et al. | 209/3.1 |
| 4,975,576 | 12/1990 | Federer et al. | 250/281 |

FOREIGN PATENT DOCUMENTS

| 0290711 | 11/1988 | European Pat. Off. . |
| 0306307 | 3/1989 | European Pat. Off. . |
| 0579952 | 1/1994 | European Pat. Off. . |
| 0579055 | 1/1994 | European Pat. Off. . |
| 0578146 | 1/1994 | European Pat. Off. . |
| 0609709 | 8/1994 | European Pat. Off. . |
| 4137912 | 5/1993 | Germany . |

Primary Examiner—Jack I. Berman
Assistant Examiner—Kiet T. Nguyen
Attorney, Agent, or Firm—McCormick, Paulding & Huber

[57] ABSTRACT

Inspection of PET bottles for contamination is performed with a mass spectrometer in which the gas sample is ionized by an ionized primary gas. This causes greatly reduced fragmentation, or unambiguous fragmentation, of the gas sample. As a consequence, the spectrum obtained is very meaningful on its own, and can be interpreted very rapidly, which is an essential prerequisite for the use of mass spectrometers in industrial inspection.

13 Claims, 2 Drawing Sheets

USE OF A MASS SPECTROMETER WITH SECONDARY IONIZATION FOR THE INSPECTION OF CONTAINERS

BACKGROUND OF THE INVENTION

The invention relates to the use of a mass spectrometer with an arrangement for selective pretreatment of a gas mixture to be analysed in order to inspect containers transported on a conveyor system, with removal from each container of at least one gas sample the mass spectrum of which is determined and evaluated.

A mass spectrometer in which the gas mixture to be analysed is ionized by primary ions of specific internal energy is known from the document EP-B 290711.

SUMMARY OF THE INVENTION

The present invention resides in method and device for inspecting gas mixtures from containers on a conveyor system. A sample of a gas mixture from each container is removed to be analyzed and is selectively pretreated prior to the analysis. The analysis is carried out on the removed samples of the gas mixture by means of a mass spectrometer after pretreatment of the sample to determine and evaluate the mass spectrum of each sample. In the device which carries out the analysis, a comparator means has a plurality of stored mass spectra against which the spectra of the gas samples are compared to determine whether the containers concerned are contaminated with foreign substances.

According to the present invention, it is now proposed to use a mass spectrometer of the type mentioned above for the inspection of containers. Such a mass spectrometer has the advantage that, owing to the very precisely adjustable "soft" ionization of the gas sample removed from the container, either no fragmentation occurs, or any fragmentation which does occur is defined with high precision. This has the advantage that the mass spectrum which is formed can be properly evaluated within a reasonable time. This makes it possible to use a mass spectrometer even in industrial inspection systems with a high container throughput, with the resultant advantages of precise determination of substances or residues in the containers. Precise and rapid determination of the spectrum with low fragmentation using such a mass spectrometer in particular allows rapid evaluation of the spectrum produced, by comparison with spectra stored in a "spectrum library". This comparison may be made by computer by a pattern-comparison technique. So-called "neural networks" or comparison systems operating with so-called "fuzzy logic" may also be used for comparing the stored spectra with the individual spectrum produced.

The mass spectrometer which has been described is preferably used in the inspection of returnable PET bottles.

Inspection of returnable PET bottles for the presence of foreign substances prior to the washing process is essential, as this type of bottle is also very useful for keeping all kinds of foreign substances. For example, this user-friendly receptacle may be used for keeping salad dressings, detergents, gasoline, engine oil, a wide range of solvents like methanol or acetone, and high-proof spirits. All these foreign substances may cause problems. Even after repeated washing and rinsing, certain foreign substances affect the taste of the newly inserted product, and may spoil a drink completely. Even though the concentrations of foreign substance remaining after the washing process are so low that damage to the consumer's health can be ruled out for all practical purposes, reliable detection of all foreign substances is essential. Undefinable tainting of fresh products invariably results in complaints by consumers.

The invention, which in principle can be used for containers of any kind, intended for holding drinks or foodstuffs or pharmaceutical products for example, will therefore now be explained in detail with reference to a PET bottle inspection machine by way of example.

BRIEF DESCRIPTION OF THE PREFERRED EMBODIMENTS

Figure 1:
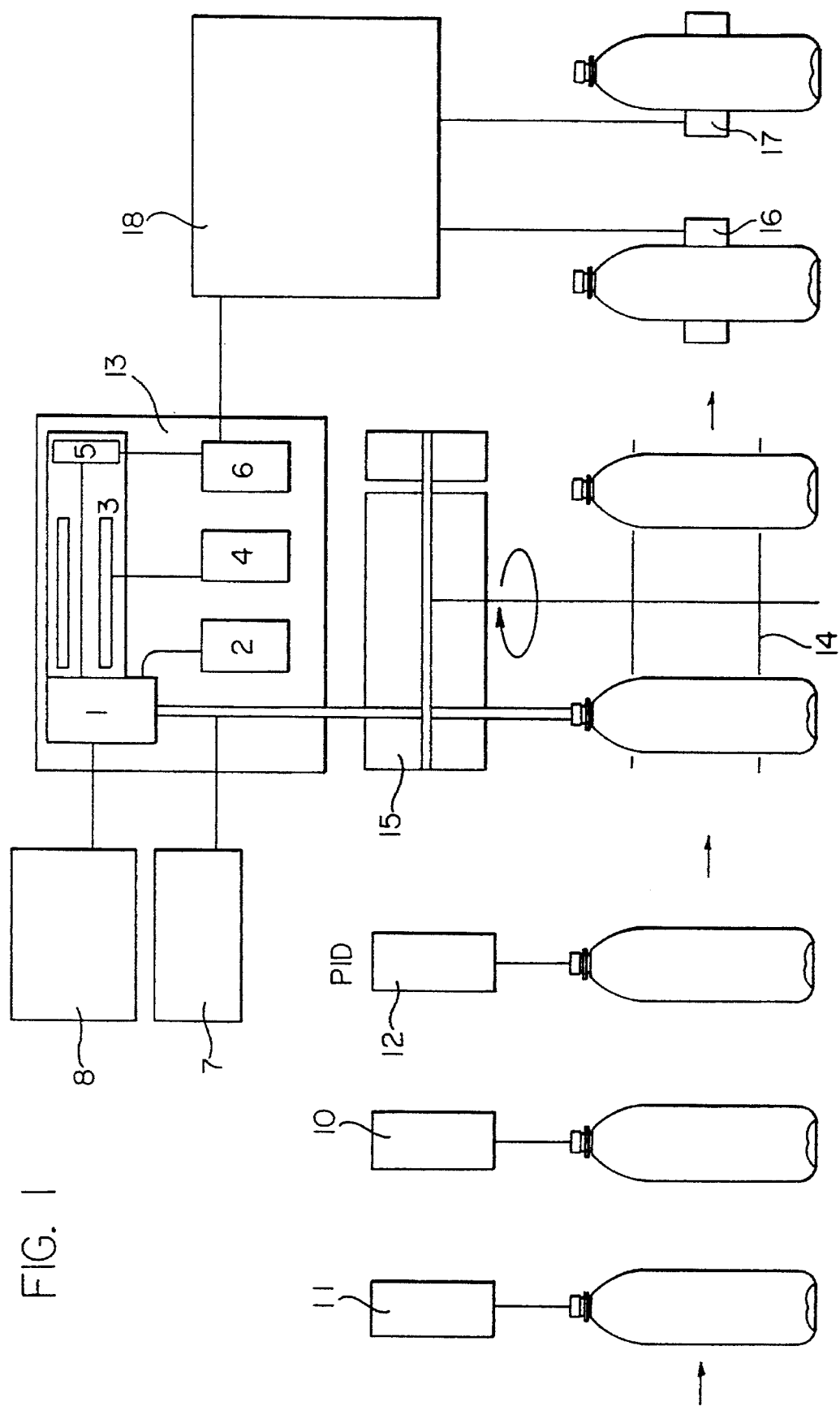
FIG. 1 shows, in highly diagrammatic form, an inspection machine with the special mass spectrometer.

The principle of the mass spectroscopy is fundamentally very simple, and is shown diagrammatically in FIG. 1. A gas sample is withdrawn from the bottle and is reduced in a series of pumping stages to a relatively low pressure of approximately $10^{-5}$ to $10^{-6}$ bar. Two oil-free low-maintenance diaphragm pumps 7 and a turbomolecular pump 8, which is likewise oil-free, are provided for this purpose. The ensuing ionization process of the sample gas must be handled very carefully if the molecules of the sample gas and also of air (oxygen, nitrogen, water vapour, carbon dioxide) are not to be fragmented, causing much information on the analysed substance to be lost. It is important that the spectrum recorded in the rapid industrial inspection should be unambiguous. For example, only positive $H_2O$ ions should be formed from the $H_2O$ contained in the gas sample, and not OH ions with the mass number 17, as ammonia ($NH_3$) also has the mass number 17 and it is essential for rapid industrial evaluation of the spectrum that the peak noted at this point should originate from ammonia only. The problems arising in the industrial use of mass spectroscopy thus differ sharply from laboratory applications in which time is available for additional differentiating analyses so that, in the stated example, the presence of OH ions can be tolerated.

Figure 2:
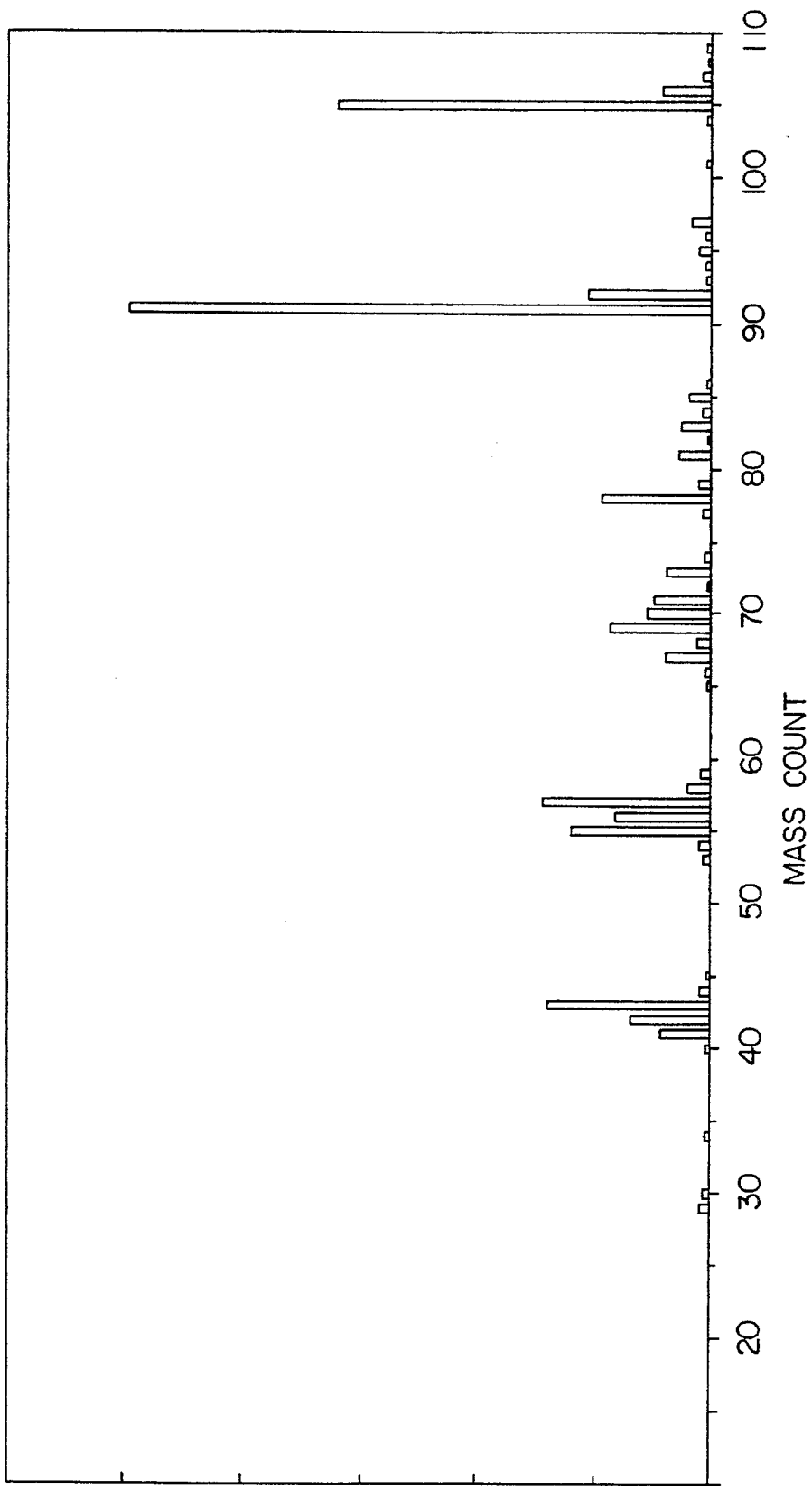
FIG. 2 shows a spectrum.

The spectrum in FIG. 2 shows the amount of information obtained in testing an individual bottle in less than 100 milliseconds (with an inspection rate of eg. 600 bottles per minute). Rapid evaluation of the spectra is preferably performed by a comparison. The fast detection algorithm is based on a library of the most important classes of substance. The measured data are processed and compared with the library. If the measured data are sufficiently close to known classes of substance, the bottle is ejected or kept on the line in accordance with the preset parameters. The algorithm is preferably designed so that unknown substances or mixtures of known substances are also evaluated correctly. For example, storing gasoline as a class of substance in the library will be sufficient to enable engine oil and diesel fuel also to be correctly identified and rejected. Unknown substances can very easily be additionally registered and stored by means of a learning function. Also, a distinction can readily be made between an orange drink and a lemon drink. In this way the carryover of flavours from previous contents can be avoided when using multi-product bottles.

The decision whether to reject a bottle is not based, as in conventional systems, upon an absence of information, but on positive identification of a substance, whether it be a harmless one which is allowed through, or a harmful one which is rejected.

Any sensitive measuring instrument has a specific memory capacity over a certain period of time, that is to say, a specific final fall time for the measured signal following a large deflection. This so-called memory effect commonly causes spurious rejections as the system cannot discriminate between supposed contamination of the preceding bottle and actual contamination of the bottle presently under test. However, the information supplied by the mass spectrometer is so well differentiated that this problem is also readily overcome. If subsequent bottles exhibit the same type of contamination at correspondingly lower levels of concentration, there is a very high probability that these are bottles whose measurement has been affected by instrument memory. They are rejected, or separately conveyed, to a repass container. This enables a repeat test of the offending bottles to be carried out.

The inspection machines for foreign substances are preferably designed as triple carousel machines with feed and discharge worm conveyors. In the feed worm conveyor, the bottles are tested for larger quantities of residual liquid and for unremoved caps (test stations 10,11). As they pass through the machine, the bottles are then tested by a high-speed PID (photo-ionization detection) probe 12. The PID probe is set to a relatively high threshold value so that only highly contaminated bottles, eg. saturated concentrations of gasoline, are detected, and spurious rejections cannot occur. This initial precheck ensures that no heavily contaminated bottles are tested with the highly sensitive mass spectrometer 13. In this way, the memory effect can largely be precluded. Relatively high concentrations which are detected by the PID probe but nevertheless cause a memory effect are identified by the spectra recognition software in the manner which has been described. All bottles which are detected while still in the feed conveyor (as having high contamination, or caps or residual liquid) are not tested by the mass spectrometer 13, but are rejected or diverted into separate containers at the machine outlet.

For the mass spectrometer, the main carousel 14 is provided with 16 stations. Sniffer tubes are contactlessly dipped into the bottles and remove air samples containing a small concentration of drink residues and any contamination present. The gas samples are drawn via a distributor head 15 into the mass spectrometer 13 and are sequentially analysed. If the throughput of bottles exceeds 18,000, bottles are analysed alternately by two separate mass spectrometers, The limit of sensitivity for gasoline is about 0.01 microliter per 1.5 liter. Ammonia can be detected down to a limit of approximately 5 ppm by weight.

The bottles are then guided through the discharge carousel into the discharge worm conveyor. Here there are two separate ejector stations 16 and 17 which separate usable bottles and those no longer usable. In addition to bottles filled with liquid and those still capped, all bottles whose testing is suspected to have been affected by instrument memory are ejected into the container for reusable bottles for a repeat inspection. Instead of ejector stations, diversion and return-feed systems may optionally be used.

The ejector stations are triggered by the control unit 18, which identifies and separates the contaminated bottles on the basis of the spectrum obtained by the mass spectrometer 13. The mass spectrometer 13 is provided in a known manner with an ionization chamber 1 in which the gas sample is ionized by means of the ionization gas from the container 2. The gas sample is ionized with primary ions under single pulse conditions at least substantially in vacuo. The ionization gas may be an inert gas, in particular xenon. A deflector unit 3 connected to a HF supply 4 guides the ions to the detector 5 and they are evaluated by the counter unit 6.

As already stated, the soft ionization of the molecules affords a differentiated and sensitive measure of the required substances. For the ionization of the sample gas molecules, the inert gas in the container 2 is ionized with electrons in the conventional manner. The inert-gas ions are selected by mass and velocity filters so that only ions possessing a specific energy, namely the discrete ionization energy, eg. approximately 12 eV, are able to react with the sample gas. This ionization process ensures that molecules of water, oxygen and nitrogen are not broken up and the entire lower measuring range therefore remains free. In this way, measurement of ammonia (mass 17) is also assured. The sample gas molecules then pass through an electromagnetic field which deflects the ions proportionally to their weight or mass. The electromagnetic field is controlled so that only one specified mass can hit the detector 5 at any given time. At the detector 5, electrical pulses proportional to the impinging ions are generated, and these are evaluated through signal processing by the spectra recognition software. Thus the reading obtained is not merely a single value for an unspecifiable contaminant. From the spectrum, it is possible to determine both the concentration and in principle the identity of the substance itself. Owing to the soft ionization, the spectrum is very meaningful on its own, and can be interpreted very rapidly, which is an essential prerequisite for the use of mass spectrometers in industrial inspection.

We claim:

1. A method of inspecting gas mixtures from containers on a conveyor system comprising the steps of:

removing from each container on the conveyor system a sample of a gas mixture to be analyzed;

selectively pretreating the gas mixture prior to analysis by ionizing primary ions under single pulse conditions at least substantially in vacuo which provides no fragmentation or a high definition reproducible fragmentation of the molecules of the gas sample, the primary ions being inert-gas ions;

analyzing the mass spectrum of the removed samples of the gas mixture by means of a mass spectrometer after the step of pretreating to determine the mass spectrum of each sample; and comparing the mass spectrum of each sample obtained in the step of analyzing the mass spectrum by a comparator means with a plurality of stored mass spectra to determine whether the container concerned is contaminated with a foreign substance.

2. A method according to claim 1, characterized in that on the basis of the evaluation the container concerned is assigned to one of at least three groups, namely, a first group consisting of containers which have been passed as satisfactory, a second group consisting of containers to be removed or a third group consisting of containers which are to undergo a repeat inspection.

3. A method according to claim 1, characterized in that the containers are drink or foodstuff containers or containers for pharmaceutical products.

4. A method according to claim 1, characterized in that the containers are returnable PET bottles.

5. A method according to claim 1, characterized in that the primary ions are xenon ions.

6. A method according to claim 1, characterized in that the primary ions have an ionization energy of approximately 12 eV.

7. A method according to claim 1, characterized in that the pretreatment of the gas sample is performed in such a way that essentially only positive $H_2O$ ions are formed from the $H_2O$ molecules contained in the gas sample, and not OH ions;

8. A method according to claim 1, further characterized by the step of analyzing the gas mixture from each container by means of a photo-ionization detector prior to analyzing the gas mixture by the mass spectrometer and preventing a container having a high concentration of a foreign substance therein from being tested by the mass spectrometer.

9. An inspection device for analyzing gas mixtures in containers which are transported through the device in a conveyor system, characterized by at least one mass spectrometer for testing and determining the mass spectra of gas mixture samples removed from each container, and a comparator means for comparing the mass spectrum obtained with a plurality of stored mass spectra to determine whether the container concerned is contaminated with foreign substances, said mass spectrometer including a means for pretreating the sample by ionizing primary ions under single pulse conditions at least substantially in vacuo, the primary ions being inert-gas ions, the means for pretreating the sample providing no fragmentation or a high definition reproducible fragmentation of the molecules of the gas sample.

10. An inspection device according to claim 9, characterized in that the primary ions are xenon ions.

11. An inspection device according to claim 9, characterized in that the primary ions have an ionization energy of approximately 12 eV.

12. An inspection device according to claim 9, characterized in that the pretreatment of the gas sample is performed in such a way that essentially only positive $H_2O$ ions are formed from the $H_2O$ molecules contained in the gas sample, and not OH ions;

13. An inspection device according to claim 9, further characterized in that a photo-ionization detection means analyzes the gas mixture prior to analysis of the gas mixture by the mass spectrometer for preventing a container having a high concentration of a foreign substance therein from being tested by the mass spectrometer.

* * * * *